(12) United States Patent
Call

(10) Patent No.: US 6,996,864 B2
(45) Date of Patent: Feb. 14, 2006

(54) CUSHION FOR A WHEELCHAIR

(75) Inventor: Evan W. Call, Bountiful, UT (US)

(73) Assignee: Otto Bock Healthcare, LP, Minneapolis, MN (US)

( * ) Notice: Subject to any disclaimer, the term of this patent is extended or adjusted under 35 U.S.C. 154(b) by 0 days.

(21) Appl. No.: 10/693,041

(22) Filed: Oct. 24, 2003

(65) Prior Publication Data

US 2004/0123391 A1    Jul. 1, 2004

Related U.S. Application Data

(60) Provisional application No. 60/421,212, filed on Oct. 25, 2002.

(51) Int. Cl.
*A61F 7/00* (2006.01)
*A61F 7/02* (2006.01)

(52) U.S. Cl. .............................. 5/653; 5/654; 5/655.4; 5/655.5; 5/655.9; 5/702; 5/909; 5/911; 297/452.27

(58) Field of Classification Search .................. 5/654, 5/653, 740, 655.9, 655.4, 655.5, 909, 702, 5/911, 737; 297/452.28, 452.27

See application file for complete search history.

(56) References Cited

U.S. PATENT DOCUMENTS

| 4,504,402 A | 3/1985 | Chen et al. |
| 5,421,874 A | 6/1995 | Pearce |
| 5,500,965 A * | 3/1996 | Hannagan et al. ............. 5/654 |
| 5,549,743 A | 8/1996 | Pearce |
| 5,562,657 A | 10/1996 | Griffin |
| 5,592,706 A | 1/1997 | Pearce |
| 6,699,266 B1 * | 3/2004 | Lachenbruch et al. ........ 607/96 |
| 2003/0026973 A1 | 2/2003 | Pause |

* cited by examiner

*Primary Examiner*—Sunil Singh
(74) *Attorney, Agent, or Firm*—Faegre & Benson, LLP

(57) ABSTRACT

A cushion for a wheelchair, including a matrix of cushion modules, wherein each cushion module includes a cushion element that has a phase change material included in its filler material that sits above an additional cushion element of a larger volume of filler material. The cushion also typically includes a support rail located on three sides of the matrix of cushion modules to align the body of the wheelchair user when sitting in the wheelchair. In addition, the cushion typically includes a base member that is positioned beneath the matrix and provides stability for the cushion. The cushion elements are typically enclosed in a moisture resistant envelope.

16 Claims, 16 Drawing Sheets

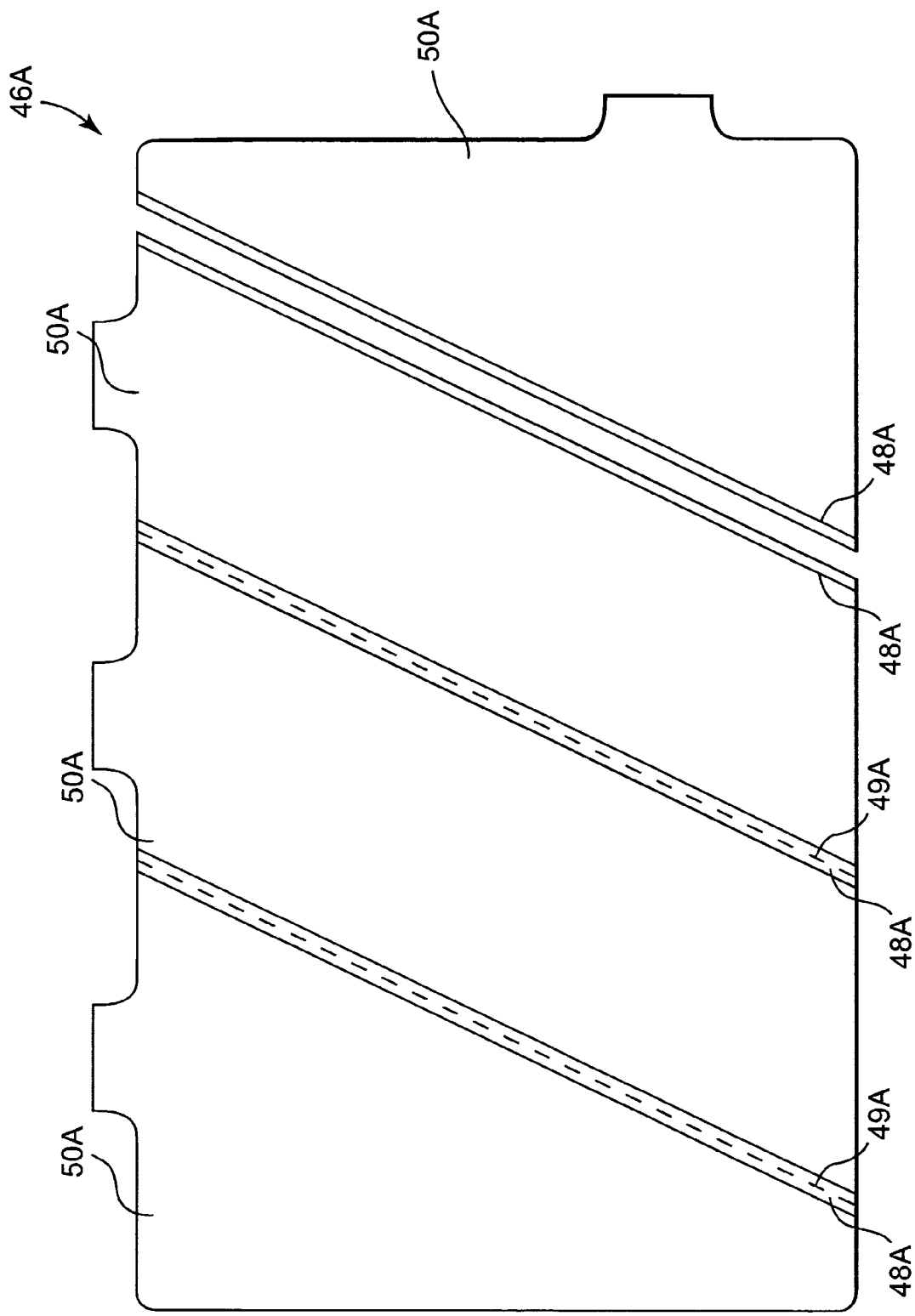

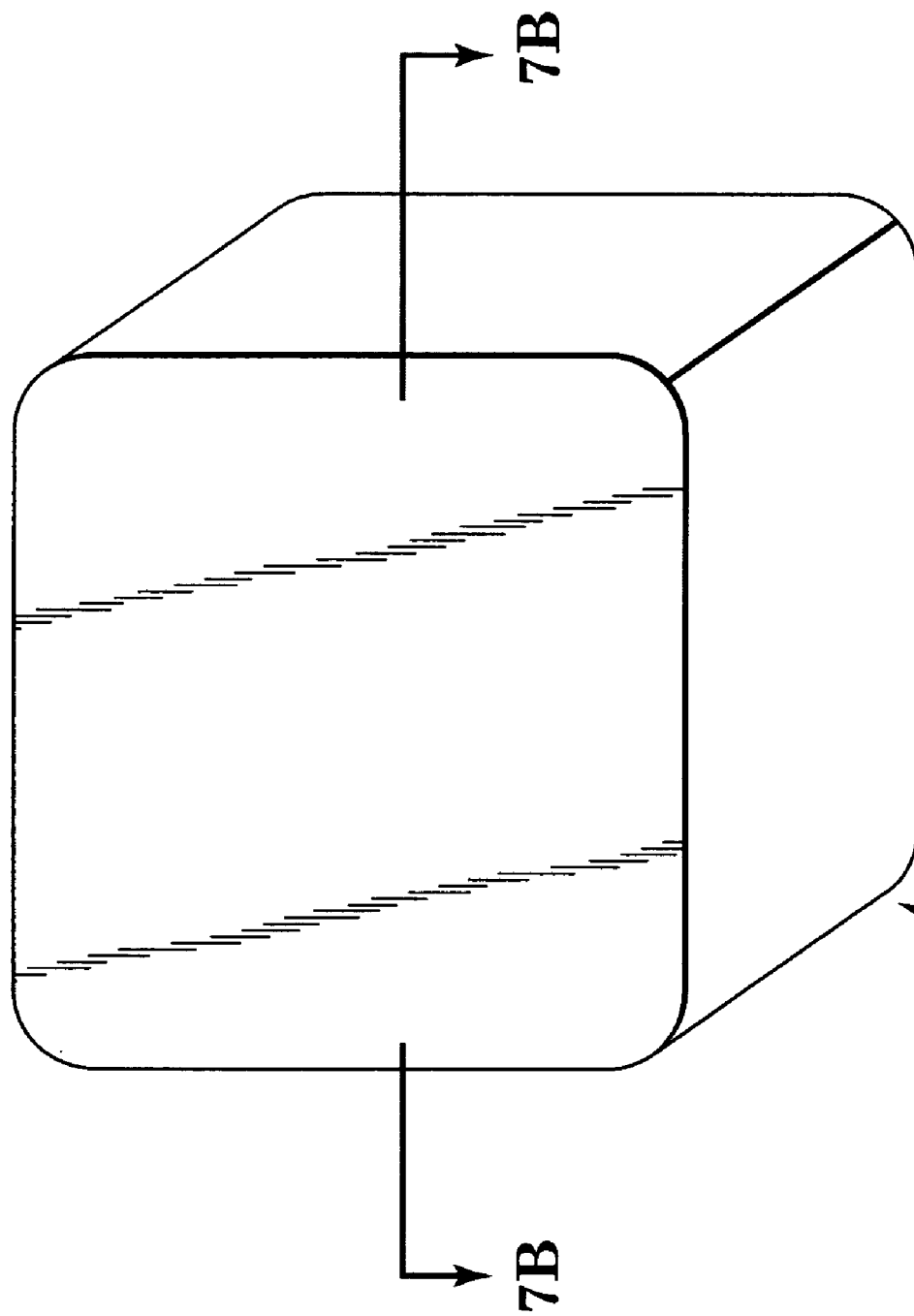

CUSHION FOR A WHEELCHAIR

This application claims the benefit of U.S. Provisional Application No. 60/421,212 filed Oct. 25, 2002.

FIELD OF THE INVENTION

The invention relates to wheelchairs. More specifically, it relates to cushions which are adapted to be used in wheelchairs.

BACKGROUND OF THE INVENTION

The prevention of the formation of pressure sores is a desirable goal when designing a wheelchair cushion. It is known that skin that is subjected to high pressure, high temperatures, moisture build up, and shear over prolonged periods of time is susceptible to tissue stress and breakdown that can cause the formation of pressure sores. While heat and moisture are generally believed to be significant factors that lead to the formation of pressure sores, the relative contribution of these factors as causative agents for pressure sores is only now beginning to be understood. There is now evidence that the presence of constant pressure on tissue combined with increasing temperature generates a proportional increase in pressure sore formation. It has been shown that increases in the moisture level generally follow rises in skin temperature, and that moisture is also a significant influence in the formation of pressure sores. Therefore, reducing skin temperature also correlates to a reduction of moisture accumulation in the seating environment, further reducing the likelihood of pressure sore formation.

The need to reduce the maximum temperature and the time averaged temperatures to which the skin is exposed is demonstrated by the fact that metabolic tissue stress increases with rising temperature. This concept is predicted by the Arrhenius equation:

$$k = A * \exp^{(-E_a/R*T)}$$

where k is the rate coefficient, A is a constant, $E_a$ is the activation energy, R is the universal gas constant, and T is the temperature (in degrees Kelvin). R has the value of $8.314 \times 10^{-3}$ kJ mol$^{-1}$K$^{-1}$.

The equation indicates that the biochemical reaction rate, and thus the cellular metabolic rate, increases as temperature increases. Application of the Arrhenius equation shows that for every 10° C. increase in temperature, the reaction rate and thus metabolic substrate requirement doubles. Correspondingly, as skin temperature goes from 28° C. to 35° C., which represents the rise of normal skin temperature in air to temperature when seated, the tissue metabolic rate would show a 50% increase. This metabolic rate increase occurs at the same time that the load created by sitting is applied to the tissue of a buttock, restricting or occluding blood flow by mechanical compression. As a result, the buttock tissue has increased demand for oxygen and metabolic nutrients, while at the same time diminishing their availability, potentially resulting in cellular metabolic deficit or cellular stress. In addition, the construction materials used in seat cushions, as well as clothing materials worn by the user or blankets, wraps, or the like, upon which the user might be seated, are typically found to be insulative, making the temperature related stress on skin under these conditions even worse. The insulative nature of these layers can, for example, maintain up to a 13° C. temperature difference between core temperature and outer layer surface temperature. Thus, a cushion that could reduce the temperature on the user's skin under these conditions would be desirable.

Stability of the wheel chair cushion is another important factor. Stability is normally defined as the ability of a cushion to maintain the cushion user in the same position as when they were seated or, at least to reduce movement of the user from the cushion. Many currently available cushions allow the user to slide, shift, or to rock from side to side during use of the wheelchair. Typically, providing stability in a proximal area, that is in the pelvic area, will improve stability throughout the lower portion of the user's body. Therefore, a cushion designed to improve the stability of the user within the wheelchair would be desirable.

SUMMARY OF THE INVENTION

The present invention is directed towards a seat cushion for a wheel chair that employs a heat absorbing material, such as a phase change material (PCM), which will interact with the user's skin to assist in removing heat and reduce the likelihood that the user will suffer from pressure sores. A cushion with a properly chosen heat absorbing material positioned within the cushion can absorb heat from the user's body despite the insulative properties of the user's clothing and outer layers of the cushion itself. One aspect of the invention includes PCM located in isolated pockets within a cushion matrix to provide effective temperature reduction and at the same preventing excessive cooling. Alternatively, the invention may include a PCM that can be located uniformly throughout the cushion or a substantial part of the of the cushion without causing excessive cooling.

Selection of the proper PCM is based on matching the temperature profiles observed in wheelchair users to the available PCMs performance ranges in combination with the use of various insulative materials that comprise the various layers of the cushion to help keep the user's skin temperature within a desired range of 30° C. to 31° C. While it is generally believed that PCMs are an acceptable heat absorbing material, other materials with heat absorbing properties may be used to achieve similar results, including, for example, urethane gels with carefully designed specific heat characteristics.

The present invention is also directed at providing improved stability for the wheelchair user when sitting in the chair. The present invention typically includes a support rail that is positioned along the perimeter of the cushion matrix at a left-side, right-side and back side of the cushion. At least a portion of the support rail on the back side has a notch or recess to provide relief for the user's sacrum. The present invention also in one embodiment includes a cushion base, which is positioned below the cushion matrix and the support rail and provides additional stability and cushioning.

BRIEF DESCRIPTION OF THE DRAWINGS

FIG. 6A is a side view of the support rail bladder, showing a portion of the support rail bladder separated into two sections along an optional perforations along a series of dividers.

FIG. 7 is an isometric view of a top and two sides of the cushion module carrier of the first embodiment.

DETAILED DESCRIPTION OF THE PREFERRED EMBODIMENTS

Figure 1:
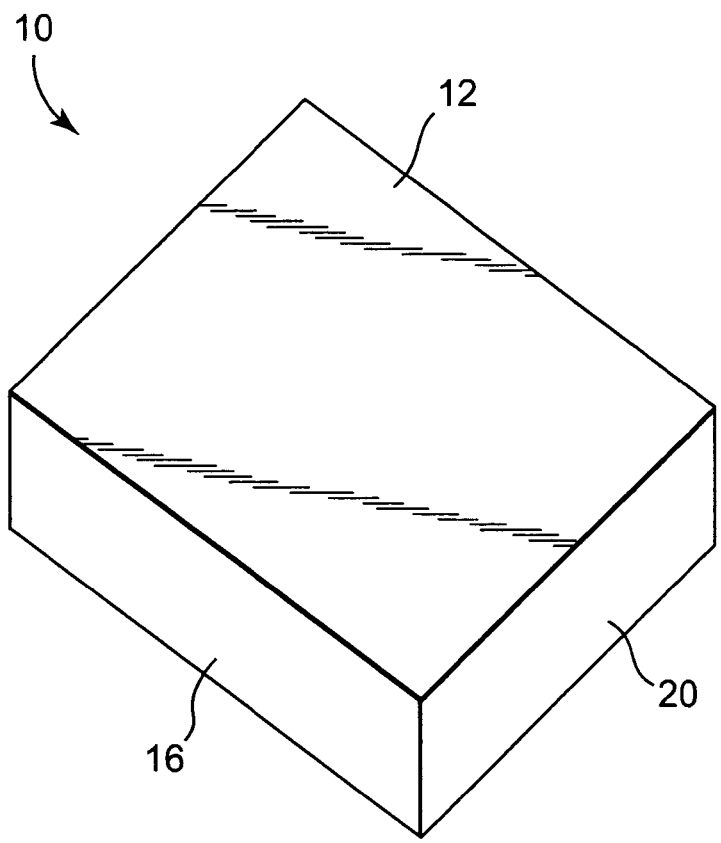
FIG. 1 is an isometric view of a first embodiment of the invention, showing top, left-side and front surfaces of a cushion.
Figure 1A:
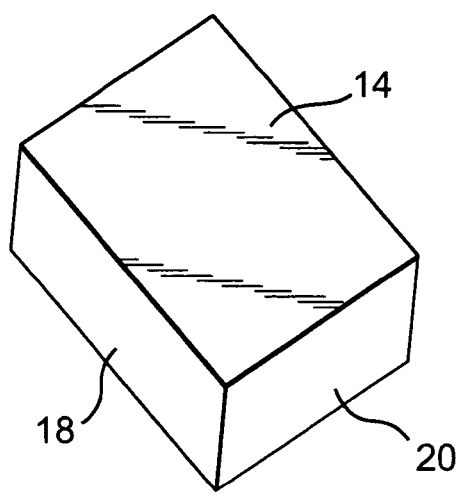
FIG. 1A is an isometric view of the first embodiment the cushion, showing bottom, right-side and back surfaces.
Figure 2:
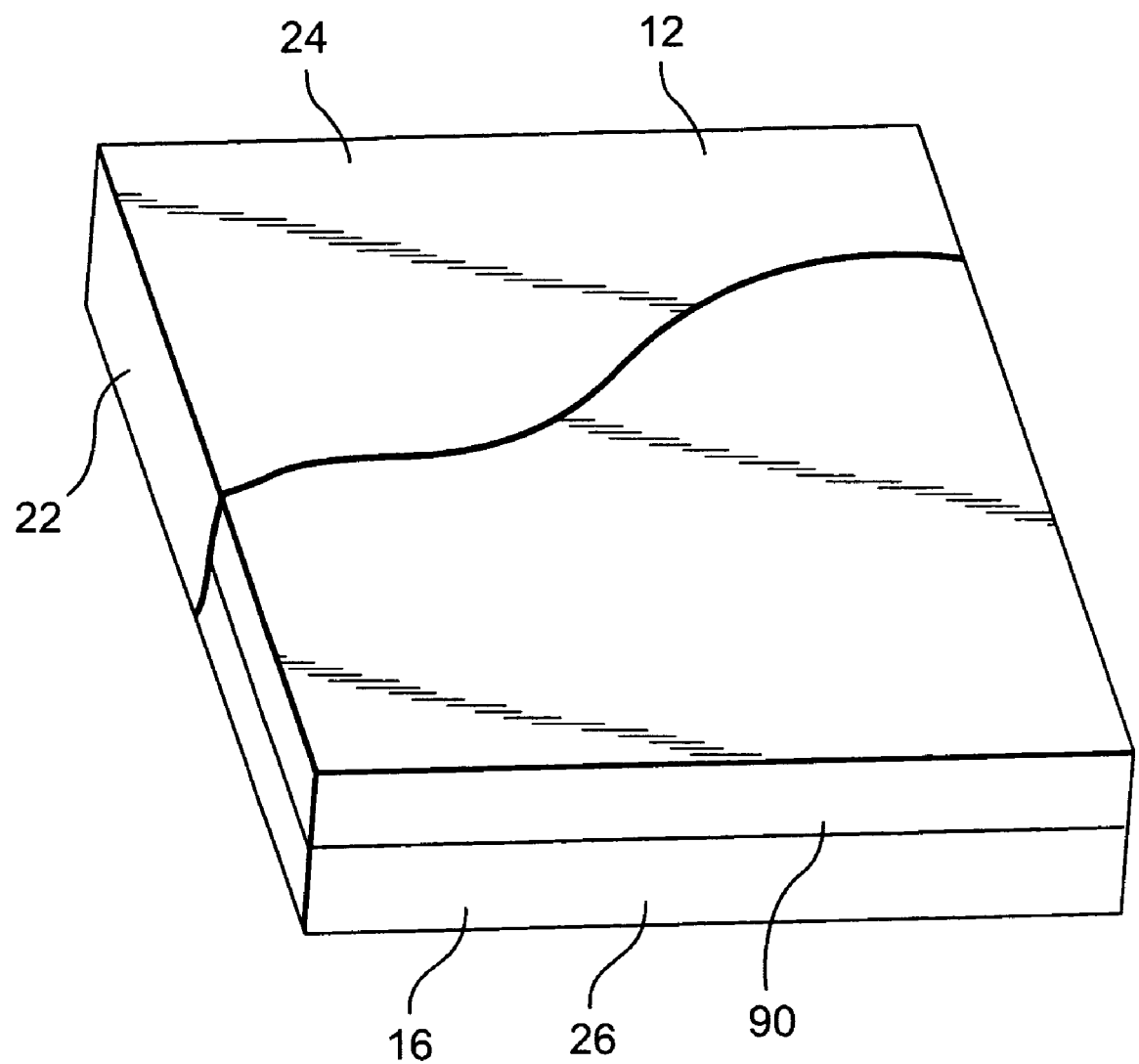
FIG. 2 is an isometric view of the first embodiment of the cushion with a portion of a cover removed, revealing a cushion base and a cushion matrix.

Referring to FIGS. 1, 1A, and 2, cushion 10 is a first embodiment of a wheelchair cushion designed to fit in a seat area of a wheelchair and be sat upon by a user of the wheelchair. Cushion 10 can have a rectangular shape, although its overall shape can be made to vary widely. Cushion 10 typically has six surfaces, defined for the purposes of this document as a top surface 12, a bottom surface 14 that opposes the top surface 12, a front surface 16, a back surface 18 that opposes the front surface 16, a left-side surface 20 and a right-side surface 22 that opposes the left-side surface 20. Cushion 10 has a width defined as a distance (typically 12–26 inches) from the left-side surface 20 to the right-side surface 22, a depth (typically 12–18 inches) defined as a distance from the front surface 16 to the back surface 18 and a thickness (typically up to 6 inches) defined as a distance from the top surface 12 to the bottom surface 14. These dimensions can be varied to suit a particular need, either over the entire cushion, or in specific portions of the cushion. Because the actual shape of the cushion may not be exactly or even approximately rectangular, the width, depth and thickness distances are to be measured from the extreme points on every defined surface.

Cushion 10 normally includes a number of internal components, including a cushion base 26 and a cushion matrix 90, each shown in block form in FIG. 2, which are located within or covered at least partially by a cushion cover 24, which is shown cutaway in FIG. 2. At least part of cushion cover 24 may be made from a moisture impervious material, such as urethane backed stretch fabric (such as Penn Nyla™), polyethylene film, polypropylene film, polyester film, or other polymeric films. In addition, at least a portion of cushion cover 24 may be made of a combination of materials, including laminates made of, for example, woven, non-woven, or other fabrics and polymeric films such as Lycra, PenNyla, Slipstop and canvas. For example, the bottom surface 14 may be made of a material that has a suitably rough finish so as to provide a substantially non-slip or slip-resistant interface to a top surface of a seat portion of a wheelchair. An example of the type of cushion cover that may be used with the current invention is disclosed in U.S. Pat. No. 5,592,706.

Cushion cover 24 may include any number of pieces of material, sewn, glued, ultrasonically welded, heat sealed, zippered, hook-and-looped, or otherwise attached together. For example, cushion cover 24 may be formed from six pieces of material, each of which substantially forms one of the six surfaces of cushion 10. Alternatively, any single piece may form part or all of one or more of the surfaces of cushion 10. Of course, it follows that a single piece may be formed and its edges attached to itself so that cushion cover 24 consists solely of that single piece and any attachment mechanisms or methods. It is to be further understood that some pieces of cushion cover 24 may overlap other pieces.

Cushion cover 24 normally includes an access structure to allow the insertion of the internal components within it. The access structure typically includes a zipper that runs along the back surface and parts of the left and right surfaces of cushion 10. When the zipper is opened, cushion cover 24 is positioned to accept the internal components. When the zipper is closed, the internal components are in one embodiment completely enclosed within cushion cover 24. Alternatively, the access structure can take many different forms, including a surface that has one or more of its edges attached to the other surfaces by hook and loop fasteners, snaps, buttons, sandwich bag-like closures, micro-replicated surfaces, or any other fastening or enclosing mechanism. The cushion cover may also include one or more pouches or pockets provided for the convenience of the user, typically attached to or integrated within the right or left surface. In addition, the cover may include flaps or straps that extend from the surfaces of the cushion that can facilitate attachment to or retention on a wheelchair seating base or structural member.

Figure 3:
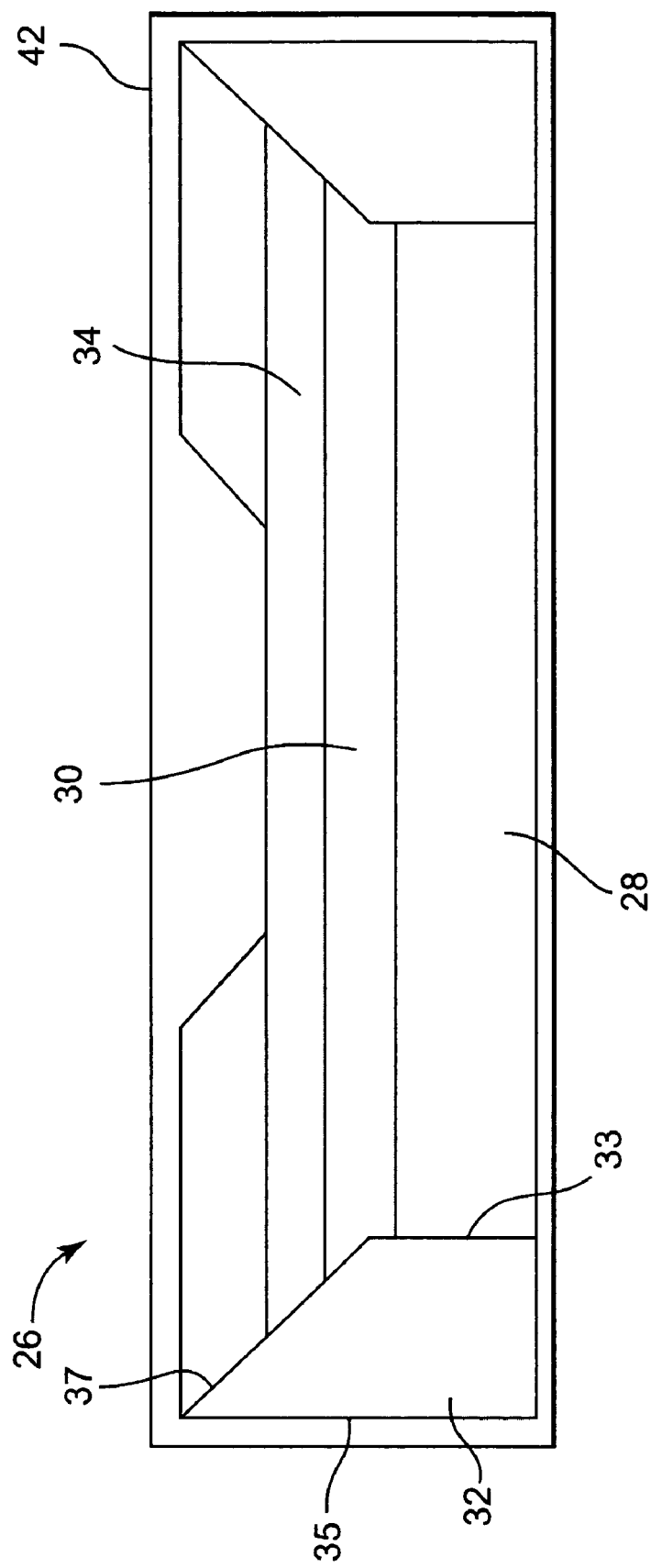
FIG. 3 is a cross-sectional front view of the first embodiment of the cushion base.
Figure 3A:
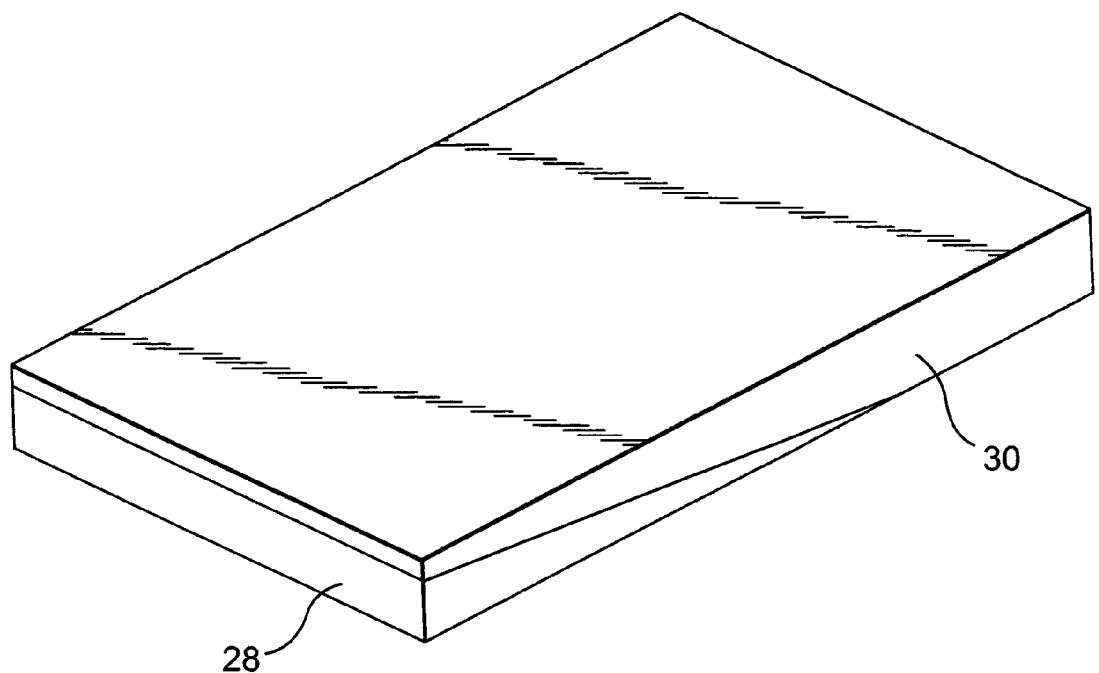
FIG. 3A is an isometric view of an interior portion of the cushion base, including and upper and lower base member.
Figure 3B:
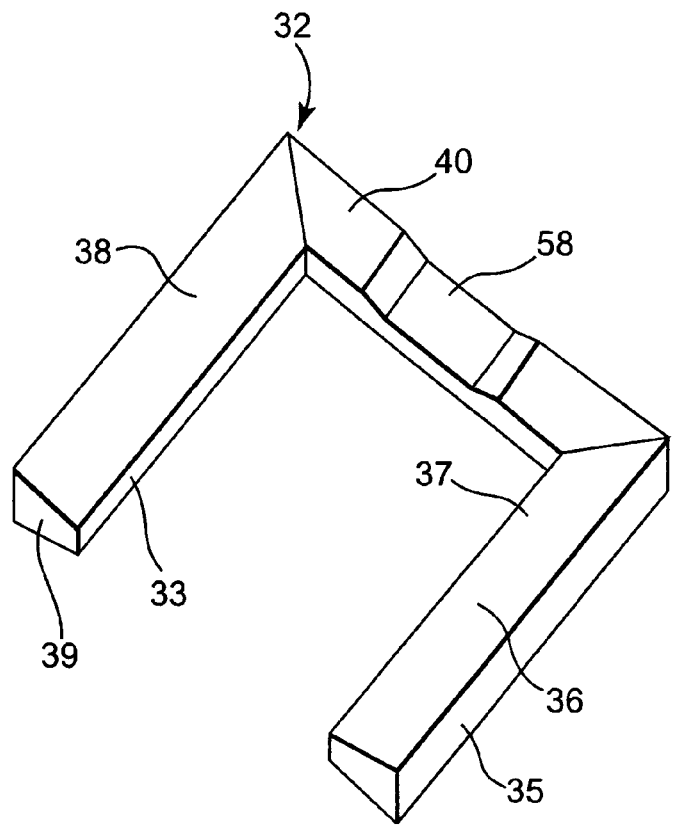
FIG. 3B is an isometric view of a outer portion of the perimeter of the cushion base.

Referring to FIGS. 3, 3A, and 3B, cushion base 26 has nearly the same width and depth as cushion 10, although its dimensions are sufficiently small enough so that cushion base 26 will fit within cushion cover 24. Cushion base 26 typically includes a lower base member 28, an upper base member 30 and an outer base member 32.

Outer base member 32 typically is a "U-shaped" component that forms left, back and right edges of cushion base 26 and can be constructed from a material such as Ethafoam™ polymeric foam from Dow. One wheelchair cushion including Ethafoam™ polymeric foam is the Cloud cushion from Otto Bock. Such a material is rigid enough to provide the cushion with stability, yet compressible to provide some cushioning effect. Outer base member 32 can have a bottom surface that is substantially flat and an outer surface 35 and inner surface 33 that are substantially straight. In the first embodiment, a distance between the inner surface 33 and the outer surface 35 of outer base member 32 is approximately one inch, although the distance between the inner surface 33 and the outer surface 35 may vary within an embodiment and/or between alternate embodiments.

Outer base member 32 has a planar top surface 37 that is typically not normal to either the inner surface 33 or the outer surface 35, and is beveled at its corners. The top surface 37 typically has a 45 degree angle from the outer surface 35 of approximately 45 degrees. In the first embodiment, the thickness of the inner surface 33 is approximately 1.25 inches. Correspondingly, the thickness of outer surface 35 is approximately 2.25 inches. It is to be understood that the angle of the top surface 37 and the thickness of the inner surface 33 and/or the outer surface 35 can be varied without departing from the scope of the invention. It is to be further understood that the outer base member 32 may take on a variety of different shapes. For example, on a portion of the back edge, the top surface 37 of the outer base member 32 may be normal to the inner surface 33 and outer surface 35 so that the height of the outer base member is, for example, approximately 1.25 inches. In another embodiment, the top surface 37 of the outer base member 32 may be normal to the inner surface 33 and outer surface 35 and an opposing bottom surface may be not normal to the inner surface 33 and outer surface 35. Alternately, the top or bottom surface may not be planar, but may have a generally decreasing height in the form of a step or steps or a concave shape, or a more irregular shape.

Outer base member 32 is formed by attaching a left base rail 36 and a right base rail 38 to a back base rail 40 with an adhesive. The mating surfaces of rails 36, 38 and 40 are typically mitered so that, when combined and attached the resultant outer base member 32 has a substantially continuous beveled top surface 37 as shown in FIG. 3B. While the top surface 37 has a continuously beveled surface from the outer 35 to the inner surface 33 over most of the outer base member 32, a portion of the back base rail 40 has a sacral notch 58, where top surface 37 is discontinuous. In the portion of the back base rail 40 that has the sacral notch, the thickness back base rail may be diminished, for example, such that the top surface 37 is normal to the inner surface 33 to the outer surface 35 so that the thickness of the back base rail 40 in this area is equal the typical thickness of the inner surface 33.

It is to be understood that outer base member 32 may be constructed of any number of components. It is to be further understood that although outer member 32 is shown as having squared corners, outer member 32 may have any shape that may define an outer shape of cushion 10, including, but not limited to, rounded corners. Lastly, each of the rails may be formed from any number of rail members.

Lower base member 28 is, in the first embodiment, constructed of Ethafoam® polymeric foam from Dow, although a number of different materials or combinations of materials may be used including other polymeric foams. Lower base member 28 has a width that is approximately equal to a distance between the inside surface 33 of the left base rail 36 and right base rail 38 that form part of outer base member 32. Lower base member 28 can have a depth of nine to ten inches, which is substantially less than the distance between the front surface 39 of outer base member 32 and the inside surface of the back edge of outer base member 32. Lower base member 28 has a maximum thickness at its front surface, the maximum thickness being in one embodiment less than the thickness of the inner surface 33 of outer base member 32. For example, the maximum thickness of lower base member 28 might be approximately 1 inch. The thickness of lower base member 28 in one embodiment tapers to a near zero thickness at its back surface. Lower base member 28 is in one embodiment attached to outer base member 32 with an adhesive between the left and right edges of lower base member 28 and the inner surface 33 of outer base member 32 so that the bottom and front surfaces of lower base member 28 and outer base member 32 are substantially flush with one another.

It is to be understood that other configurations of lower base member 28 may be acceptable. For example, lower base member 28 can be constructed of any number of individual components or molded as a single unit. Alternatively, lower base member 28 may be integrated into the outer base member 32 or any number of pieces that are assembled to form the outer base member 32. The structure formed by the attachment or integration of lower base member 28 and outer base member 32 provides a unique pelvic captivation structure, which provides desired improved stability.

Upper base member 30 is typically constructed of urethane, although other materials may be used. Examples of possible materials include light weight compressible elastomeric plasticized styrenic triblock co-polymers, a conglomeration of small displaceable pellets or beads of cushioning materials, gels or elastomers (e.g. Technogel™) or zero memory materials (e.g. Floam™). Upper base member 30 has a width that is in one embodiment approximately equal to that of lower base member 28 and a depth approximately equal to the distance between the front surface 39 and the inner surface 33 of the back rail 40 of outer base member 32. Upper base member 30 is shown in FIG. 3 as having a thickness at its front surface approximately equal to, although slightly larger than, a difference of the thickness of the inner surface 33 of outer base member 32 and the thickness of lower base member 28 at its front surface. The thickness at the front surface of upper base member 30 may be substantially more or less than said difference. The thickness of upper base member 30 typically increases along a taper on its bottom surface running from its front surface along the depth of upper base member 30 that is approximately complementary to the taper on lower base member 28 until the thickness of upper base member 30 is approximately equal to the height of the inner surface 33 of outer base member 32, starting at the back surface of lower base member 28. Upper base member 30 in one embodiment has a substantially constant thickness on its remaining depth to its back surface. This constant thickness may be more or less than the height of the inner edge of outer base member 32. It is to be further understood that the thickness of the upper and lower base members can vary without departing from the scope of the invention.

Upper base member 30 is in one embodiment attached to lower base member 28 with an adhesive along the top surface of lower base member 28 and the tapered portion of the bottom surface of upper base member 30. Upper base member 30 may also be attached to the inner surfaces of outer base member 32 along the left right and back surfaces of upper base member 30. The combination of lower base member 28 and upper base member 30 can have a substantially rectangular cross-section so that, when attached to outer base member 32, resulting in a bottom surface that is substantially even. It is to be understood however, that upper base member 30 is not necessarily attached to either lower base member 28 or outer base member 32. Upper base member 30 may merely be located within cushion 10 so that it rests approximately in relation to lower base member 28 and outer base member 32 as described above.

Referring again to FIG. 3, cushion base 26 may further include a base fill member 34, which is located on top of upper base member 30. Base fill member 34 is a substantially flat, thin sheet of urethane or other material that has the substantially same width and depth as upper base member 30. Base fill member 34 may be attached to upper base member 30 with a suitable adhesive. Possible adhesives include 3M Spray Foam Adhesive, 3M Super 77 Spray Adhesive, Sure bonder 355 Spray adhesive and 3M Fastbond Foam adhesive 100 (water based). Alternatively, base fill member 34 is not attached to upper base member 30 or is attached with another suitable mechanism.

Cushion base 26 is typically surrounded with a base cover 42, which substantially encloses cushion base 26. Base cover 42 is in one embodiment constructed of a flexible, moisture-impervious material such as a thermo-plastic, urethane, neoprene, poly-isopropylene, or other suitable material. Base cover 42, for example, may include two sheets of such material and an attachment structure so that cushion base is substantially enclosed and sealed within base cover 42. The attachment structure may include an adhesive, ultrasonic or heat weld, or any other suitable structure.

Figure 5:
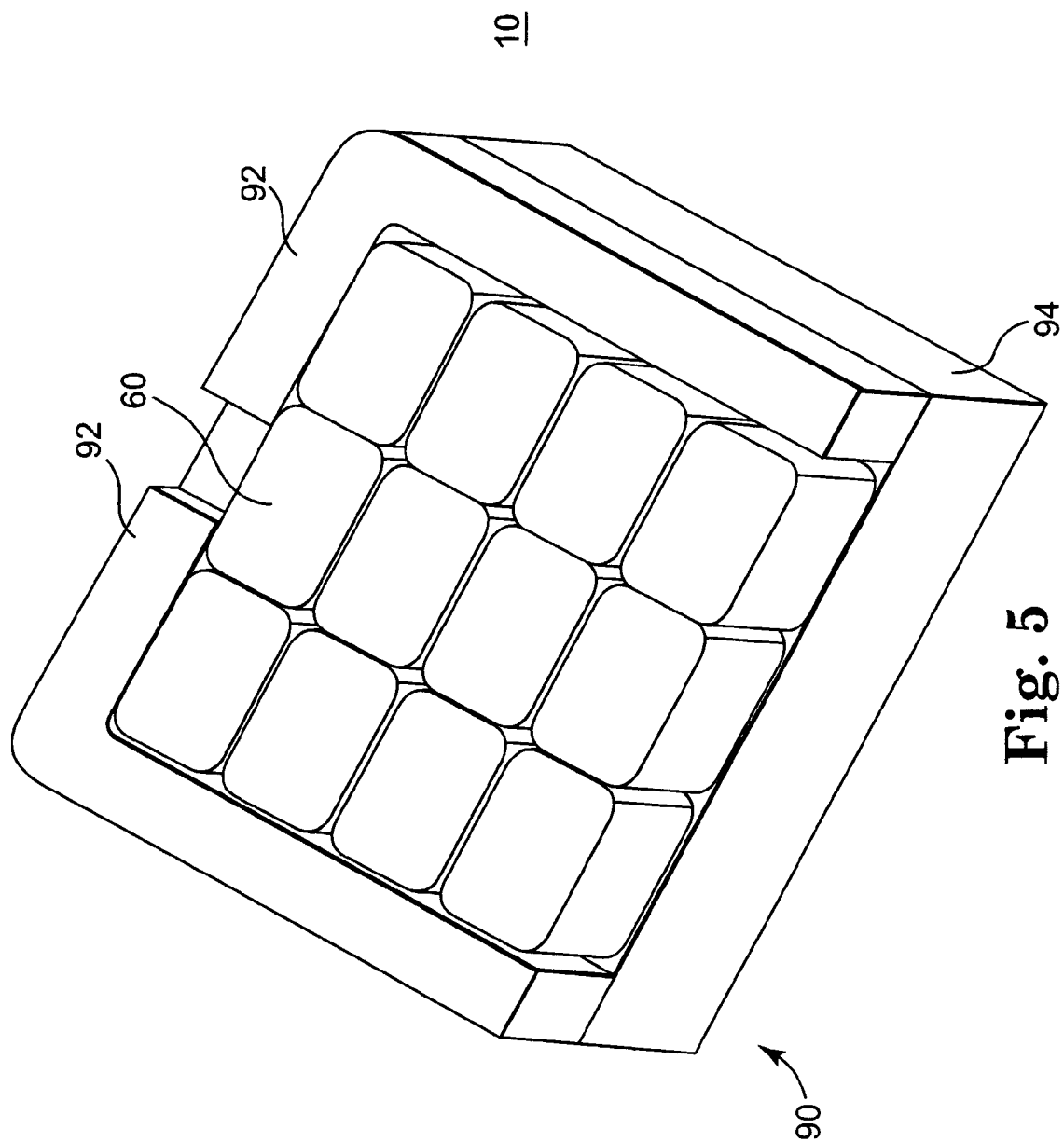
FIG. 5 is an isometric view of the cushion matrix of the first embodiment, showing a base carrier attached to the support rail and cushion module carriers.

Referring to FIGS. 2 and 5, cushion matrix 90 is typically positioned above cushion base 26 within cushion 10. In the first embodiment, cushion matrix 90 includes several cushion modules 60. In addition, it may include two support rails 92, which typically substantially surround the several cushion modules 60 on their left, right and back sides. The combination of the support rails and cushion modules that make up the cushion matrix 90 are arranged and attached to each other to form cushion matrix 90, although attachment is not necessary. In the first embodiment, each support rail and cushion module includes at least one cushioning element and a carrier, which is constructed to accept the cushioning element.

Cushion matrix 90 may also include a base carrier 94, which is designed to fit over and accept cushion base 26. Base carrier 94 can be comprised of a flexible, stretchable and breathable fabric assembly, that can be attached to the perimeter of the combination of cushion modules, and shaped and formed to accept cushion base 26. Typically, the fabric selected for the base carrier 94 is the same as that selected for the cushion module carrier 62, although other suitable fabrics may be used such as a Nylon stretch knit also known as Lycra®. Each carrier is typically constructed so that it is properly sized and shaped to provide an internal volume that can accept appropriate cushioning elements. In addition, each carrier typically is constructed with an aperture or other appropriate device to allow insertion or removal of the cushioning elements from the carrier.

As shown in FIG. 5, each support rail 92 is sized and located such that it is positioned along the entire depth of the cushion 10 and extends approximately three inches along the width of the left or right edge of the cushion 10 as well as extending approximately three inches along the back edge of cushion 10. Typically, no support rail 92 extends through the middle portion of the width of the back edge of the cushion 10 that coincides with the portion of the back base rail 40 where the top surface 37 is discontinuous. As described above, this structure is generally included to provide sacral support for the user while at the same time the notch forms a cutout for the sacrum and reducing the possibility of point loading. A filler of lighter, more compressible material than the rails may be placed in the notch region to provide further sacral support at the notch.

It is to be understood that the support rails 92 may have alternate arrangements without departing from the scope of the invention. For example, the support rail may rest upon any or all portions of the left, right and back edges of the cushion base 26, including the portion which has been descried as the sacral notch. In addition, while the support rail 92 is typically sized and located so that it extends along the outermost three inches of the left, right and back edges of the cushion, the exact size and location of the support rails 92 may vary along different parts of a cushion or along the entire cushion.

Each support rail 92, in one embodiment, includes a support rail carrier 44. As described above, support rail carrier 44 normally includes an access mechanism such as aperture 56, formed into support rail carrier 44 by any suitable means, or any other mechanism that allows access to an internal volume of support rail carrier 44.

Figure 6:
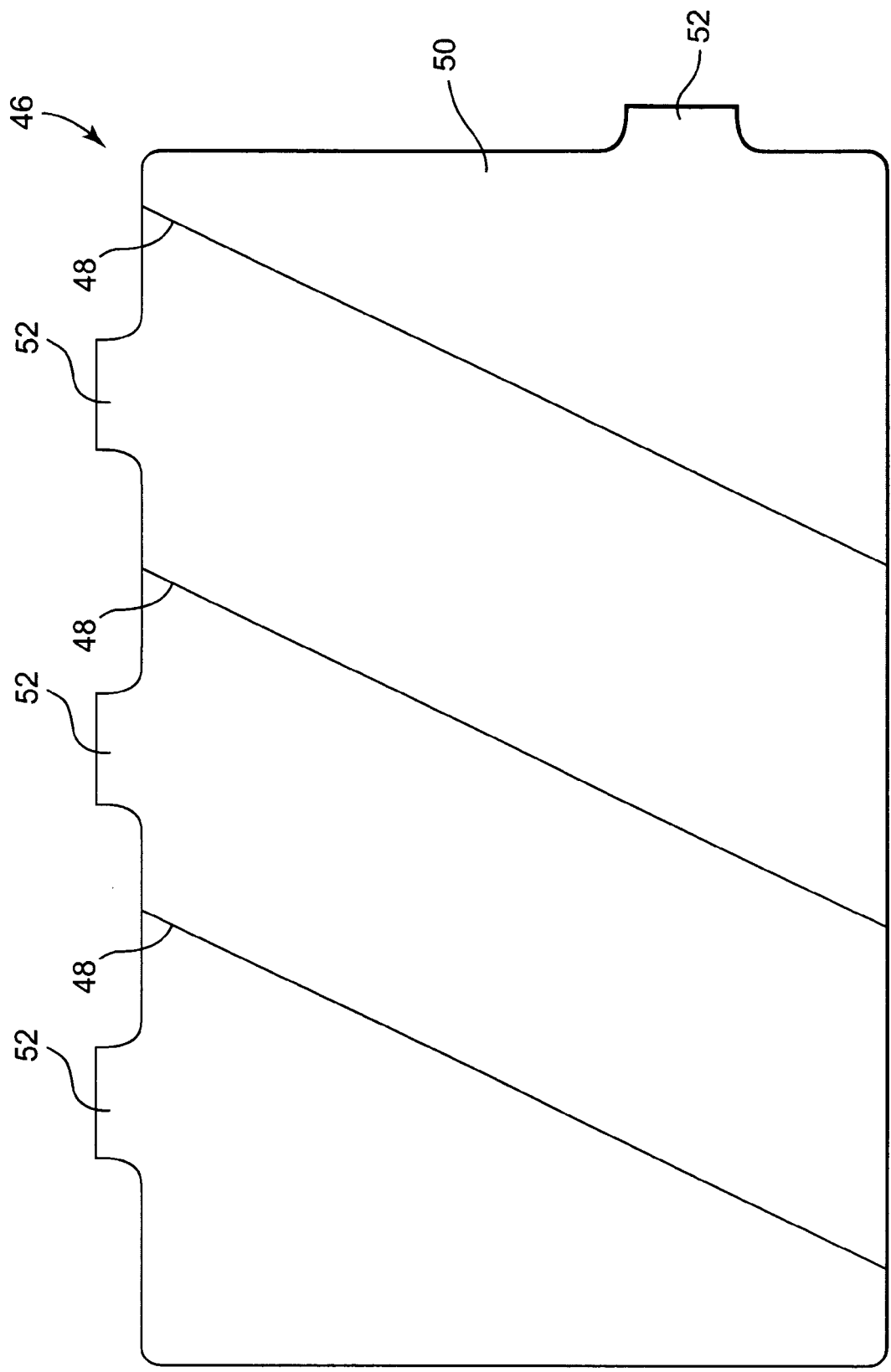
FIG. 6 is a side view of a support rail bladder of the first embodiment, designed to accept cushion material and sized to fit within a support rail carrier.

Support rail 92 typically includes at least one support rail bladder 46 shown in FIGS. 6 and 6A. A typical cushion 10 can have two or more support rail bladders, with one or more located on each of the left and right edges of the cushion and each support rail bladder shaped to form at least a portion of the back edge of the cushion. Any number of support rail bladders of similar or varying shapes and sizes may be included to create the support rail 92. The typical support rail bladder 46 includes a substantially rectangular bladder and is, in one embodiment, made of a flexible moisture-impervious material such as urethane. Further, the support rail bladder 46 may include one or more dividers 48, which can partition the support rail bladder 46 into a plurality of discrete chambers 50. Typically, divider 48 has a 45 degree angle with respect to the centerline of support rail bladder 46, although the divider may have any angle without departing from the scope of the invention. The dividers 48 may be formed by welding the bladder to itself in specific locations using an ultrasonic or radio frequency welding process so that the discrete chambers are substantially sealed with respect to one another. Alternatively, the dividers may be formed by using any adhesive, bonding process, or any other suitable structure that will separate the said rail bladder into discrete chambers.

Further, each chamber may be constructed so that it has a mouth 52, which provides access to the internal volume of the chamber so that each chamber 50 can accept a filler material within the internal volume. Typically, each chamber can be filled with an amount of filler material such as Floam or other similar material through a mouth 52.

When a chamber 50 has received filler material through mouth 52, mouth 52 can be subsequently sealed with a structure, in one embodiment, similar to those that can be used to create divider 48. While the volume of each chamber 50 may be identical to every other chamber 50, it is to be understood the volume of each chamber 50 and the amount of filler located within each chamber may vary with respect to other chambers. It is to be further understood that while the first embodiment shows a single support rail bladder 46 in each support rail, each support rail may include any number of support rail bladders, each of which may include any number of chambers, which may allow for varying the relative amount of fill in the right or left rail 92. For example, as shown in FIG. 6A, any or all dividers 48A may each include a perforation 49A to allow the separation of one or more of the individual chambers 50A of support rail bladder 46A from each other.

The support rail carrier 44 typically accepts the support rail bladder 46 through the aperture 56. The use of a support rail bladder 46 with multiple chambers 50 allows the support rail bladder to be more easily positioned evenly within the support rail carrier 44. In addition, the plurality of chambers prevents the filler material from congregating in any one particular area of the support rail and thereby provides for a more consistent shape throughout the support rail. Once the support rail bladder is accepted within the support rail carrier, it is typically positioned so that it has a substantially consistent cross sectional area throughout the support rail, although it alternatively may have a significantly varying cross sectional area in different parts of the support rail.

Figure 7B:
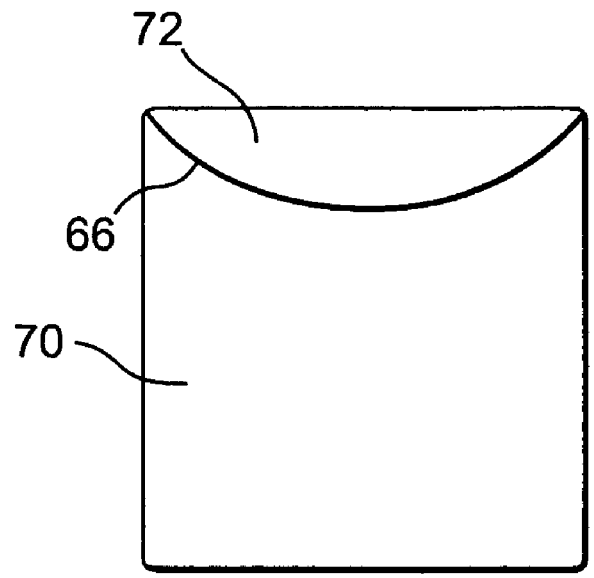
FIG. 7B is an isometric view of a bottom and two side so the cushion module carrier of the first embodiment, showing the primary interior volume and an aperture for access to the secondary interior volume.
Figure 7A:
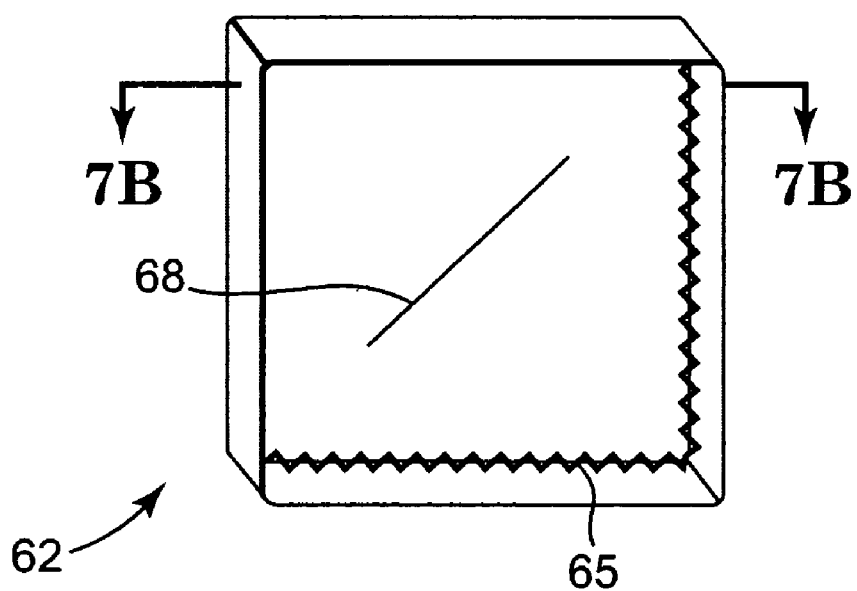
FIG. 7A is a cross-sectional side view of the cushion module carrier of the first embodiment, showing primary and secondary interior volumes.

Referring to FIGS. 7, 7A and 7B each cushion module 60 in the first embodiment includes a cushion module carrier 62. Cushion module carrier 62 is typically constructed from one or more flexible, stretchable, and breathable fabric pieces, such as a Nylon stretch knit also known as Lycra®, and can have a rectangular cross-section, as shown in FIG. 7B, although its shape may vary somewhat. The typical cushion module carrier 62 has an internal partition 66, normally formed of similar fabric material as the outside surfaces, attached into the interior of cushion module carrier 62 along stitch pattern 65. While the internal partition 66 is sewn to the cushion module carrier 62, in one embodiment, other attachment mechanisms can be used. Internal partition 66 divides the resultant interior volume of cushion module carrier 62 into a primary internal volume 70 and a secondary internal volume 72. An aperture 68 is formed into internal partition 66 by any appropriate means to provide access to the secondary internal volume 72. Alternatively, any structure that provides a divided volume within the cushion module carrier and access to the volume partitions may be used.

Figure 9:
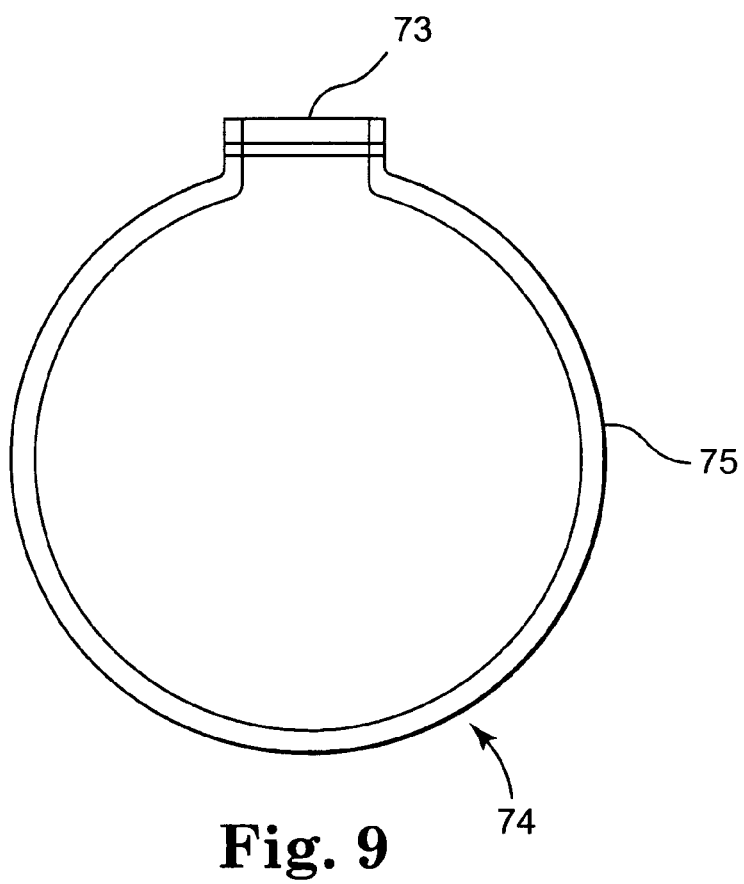
FIG. 9 is a side view of a cushion bladder of the first embodiment, designed to accept thermal transfer and/or cushion material and sized to fit within the primary or secondary interior volume of the cushion module carrier.

Each cushion module 60 also typically includes a thermal transfer element 74 and a cushion element 76. Referring to FIG. 9, thermal transfer element 74 includes a bladder typically constructed of a flexible, substantially moisture-impervious material such as urethane. Typically, the bladder is constructed of a number of pieces of urethane that are attached to each other to form a bladder with an internal volume. The urethane pieces are attached to each other using any acceptable bonding or adhesive methods or structures. For example, the pieces may be ultrasonically welded to form a seam 75. The resulting bladder typically has a mouth 73, which provides access to an interior volume so that the bladder can accept a filler, such as a phase change material, within the internal volume. After an amount of filler material has been placed inside of the thermal transfer element, the mouth 73 can be sealed using a bonding or adhesive method or structure similar to that used to form the interior volume of the thermal transfer element resulting in a substantially sealed element.

Thermal transfer element 73 typically includes a heat absorbing material, such as a phase change material (PCM), which is placed inside of the bladder. PCMs function by melting from a solid to a liquid, and in the process, absorbing heat. There is typically a difference between the melting point and the re-crystallization point of five to six degrees Celsius. It is desirable to use a PCM that maximizes heat absorption performance in a desired temperature range (endothermic part of the temperature cycle) while not increasing heat exposure on the lower end (exothermic part of the temperature cycle). By use of such a PCM, or combination of PCMs, the body temperature and, by association, the accumulation of body moisture or sweat is reduced and the occurrence of related pressure sores is thereby reduced. Note that the heat absorbing material can be selected with reference to desired clothing layers to be worn by the user in order to achieve a desired temperature profile.

Currently, paraffin based PCMs are preferred due to their ease of incorporation into a cushion. The preferred PCM comes from the group of tetradecane, pentadecane, hexadecane, heptadecane, octadecane, nonadecane, eicosane, heneicosane and docosane. Of this group, octadecane and less so eicosane are particularly preferred at this time because of its performance and price. Nonadecane provides better performance, but is not readily available at low cost. Another preferred material is TH29, a naturally occurring hydrated calcium carbonate salt that melts at 29° C. and absorbs 170 kj/kg heat. A list of paraffinic and non paraffinic PCM materials is attached as Table 1 and Table 2, respectively.

Because the PCMs mentioned above have a tendency to conglomerate with successive melt and freeze cycles, microencapsulation of the PCM material and mixture with a material that prevents such conglomeration is desirable. Accordingly, Frisby Inc. Thermasorbe 83 (T83), a microencapsulated octadecane was chosen as the preferred PCM. The T83 was mixed with a Floam lubricant as described in U.S. Pat. Nos. 5,421,874, 5,549,743, 5,592,706 and 5,562,657, to create a slurry of PCM material used in the thermal transfer element 74. Generally, surfactant and viscosity modified water based solvent or friction and viscosity modified oil based solvents would work well with an insoluble PCM. Alternatively, the PCM could be mixed with other fill materials such as particulates, beads, gels or fluids.

Figure 4:
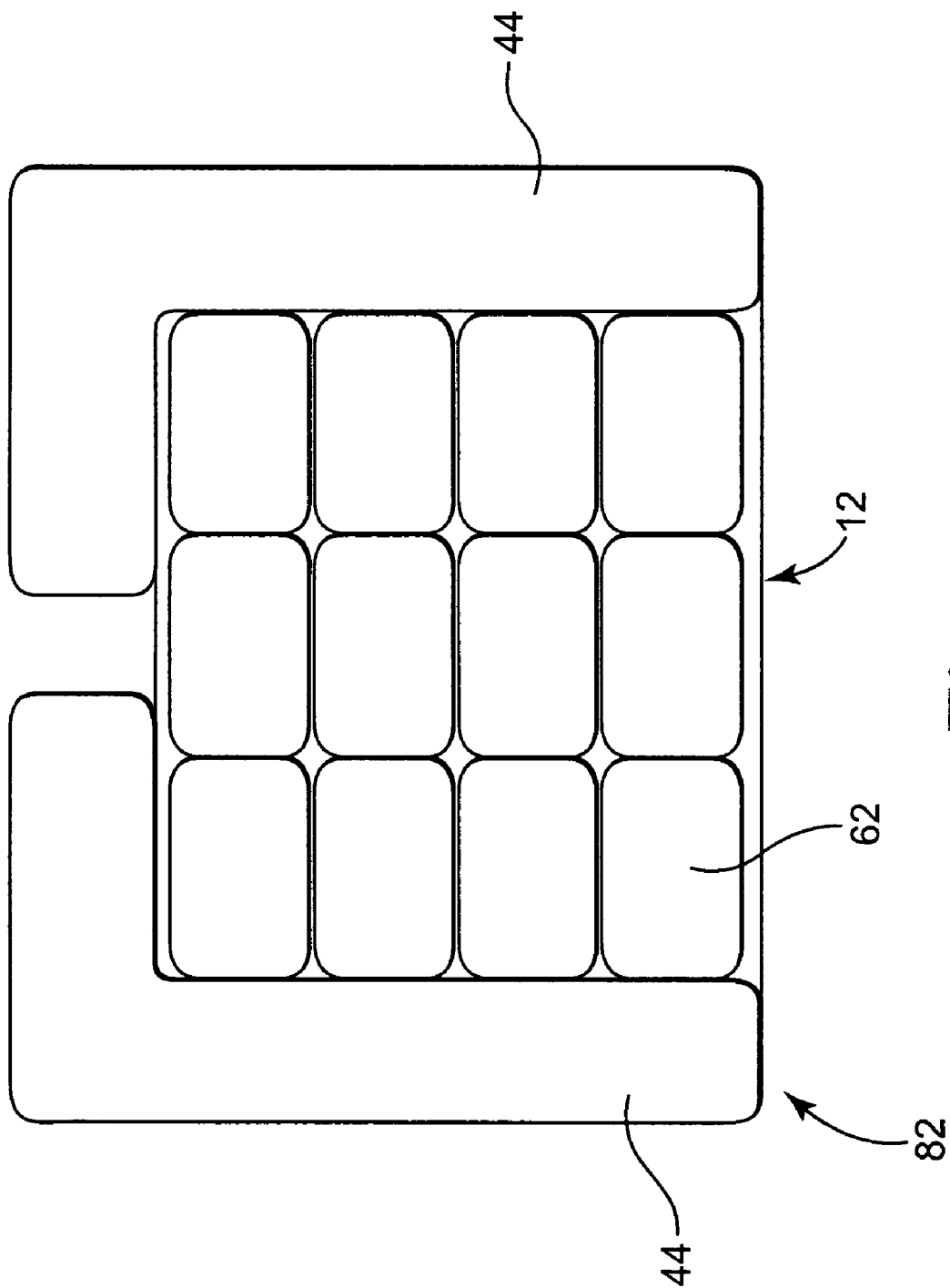
FIG. 4 is a top view of the cushion matrix of the first embodiment, showing support rail and cushion module carriers.

Referring to FIG. 4, carrier matrix 82 refers to a collection of carriers that are a part of cushion matrix 90. In the first embodiment, carrier matrix 82 includes two support rail carriers 44, and a collection of cushion module carriers 62. In the first embodiment, each of the cushion module carriers 62 are substantially the same size and are arranged and attached together in a generally rectangular pattern. In addition, each of the support rail carriers 44 are arranged and attached to the collection of cushion module carriers so that one edge of the support rail carriers 44 is even with the edge of the cushion module carrier collection that is closest to the front surface 12. The support rail carriers 44 are collectively attached along the left, right and a substantial portion of the back sides of the collection of cushion module carriers. It is to be understood that while a collection of cushion module carriers are shown in FIG. 4, any number of cushion module carriers may be used. For example, a single, appropriately sized, cushion module carrier may be used.

Figure 8:
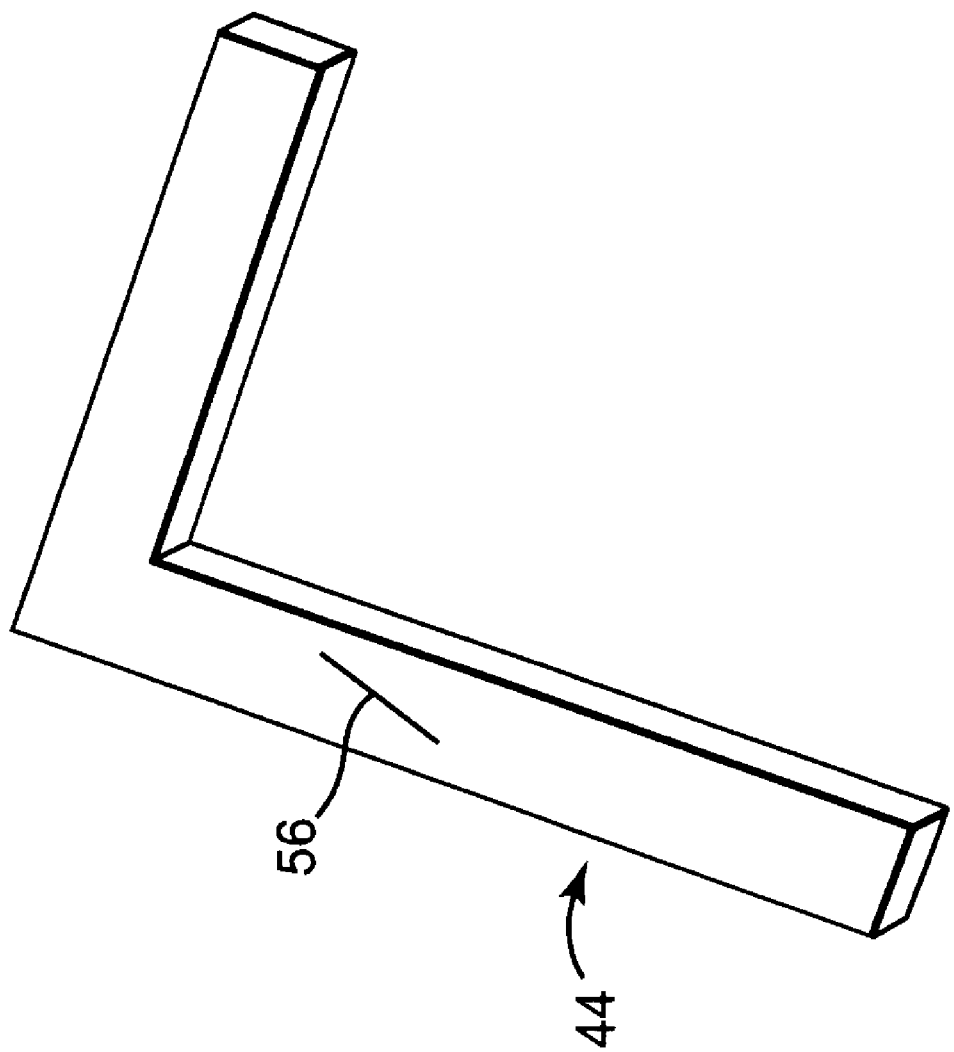
FIG. 8 is an isometric view of a portion showing the bottom and two sides of a portion of the support rail carrier of the first embodiment.
Figure 11:
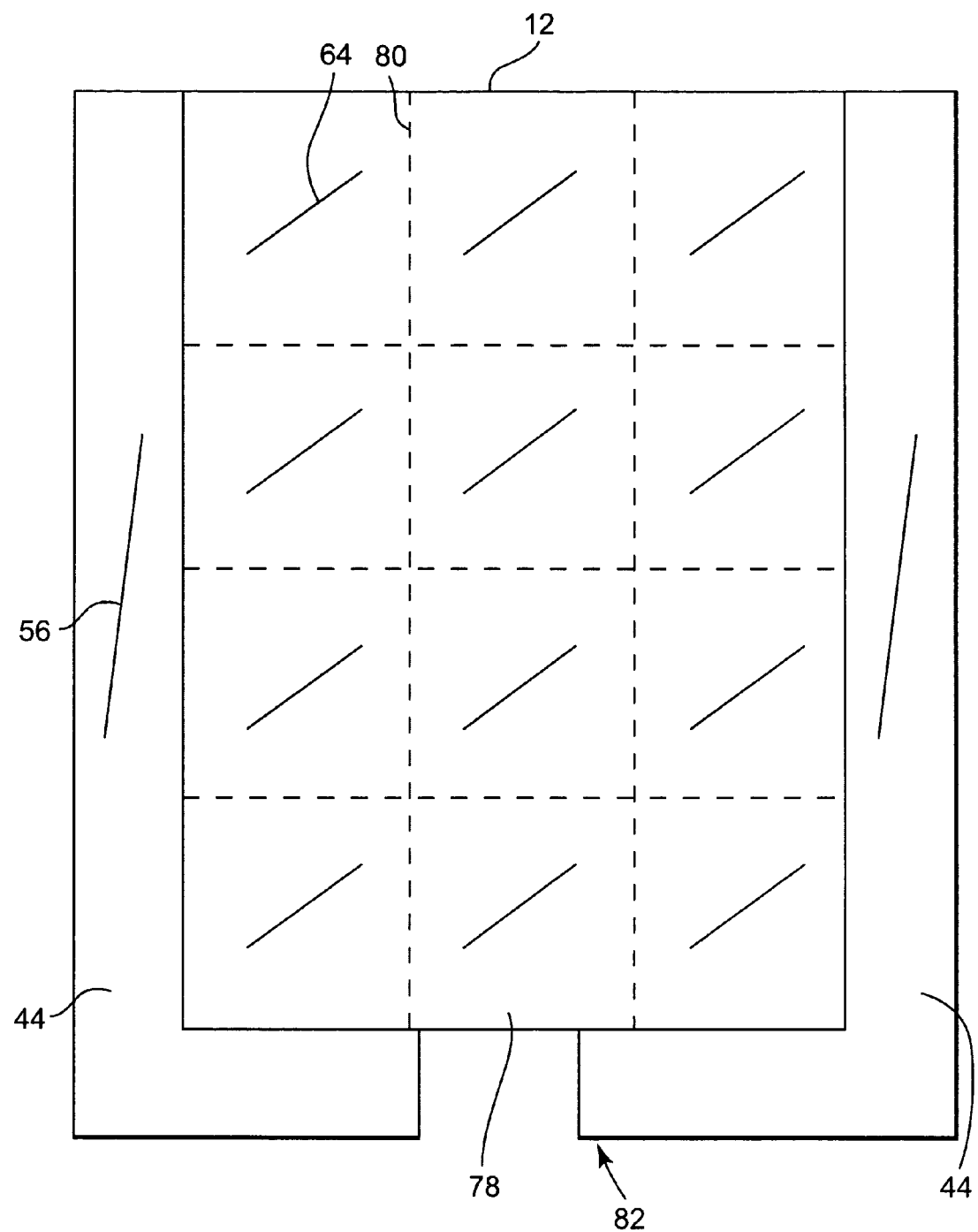
FIG. 11 is a bottom view of a portion of the cushion matrix of the first embodiment, showing support rail and cushion module carriers.

The bottom surface of cushion module carrier 62 may be formed from a discrete piece of similar fabric. Referring to FIG. 11, the bottom of each cushion module is in one embodiment a bottom surface matrix 78, formed from a single piece of similar fabric as cushion module 62, which provides a bottom surface for each cushion module carrier 62. Bottom surface matrix 78, as shown in FIG. 11, can include a stitch pattern 80 that connects each cushion module carrier 62 to bottom surface matrix 78. Bottom surface matrix 78 also can include a collection of apertures 64, formed into surface matrix 78, each of which allows access to a primary internal volume or a cushion module carrier. Each support rail carrier 44 has an aperture 56 formed into its bottom surface to allow a support rail bladder 46 (see FIGS. 6 and 8) to be inserted into it. Support rail carriers 44 are normally attached to bottom surface matrix 78 to substantially form carrier matrix 82.

Figure 12:
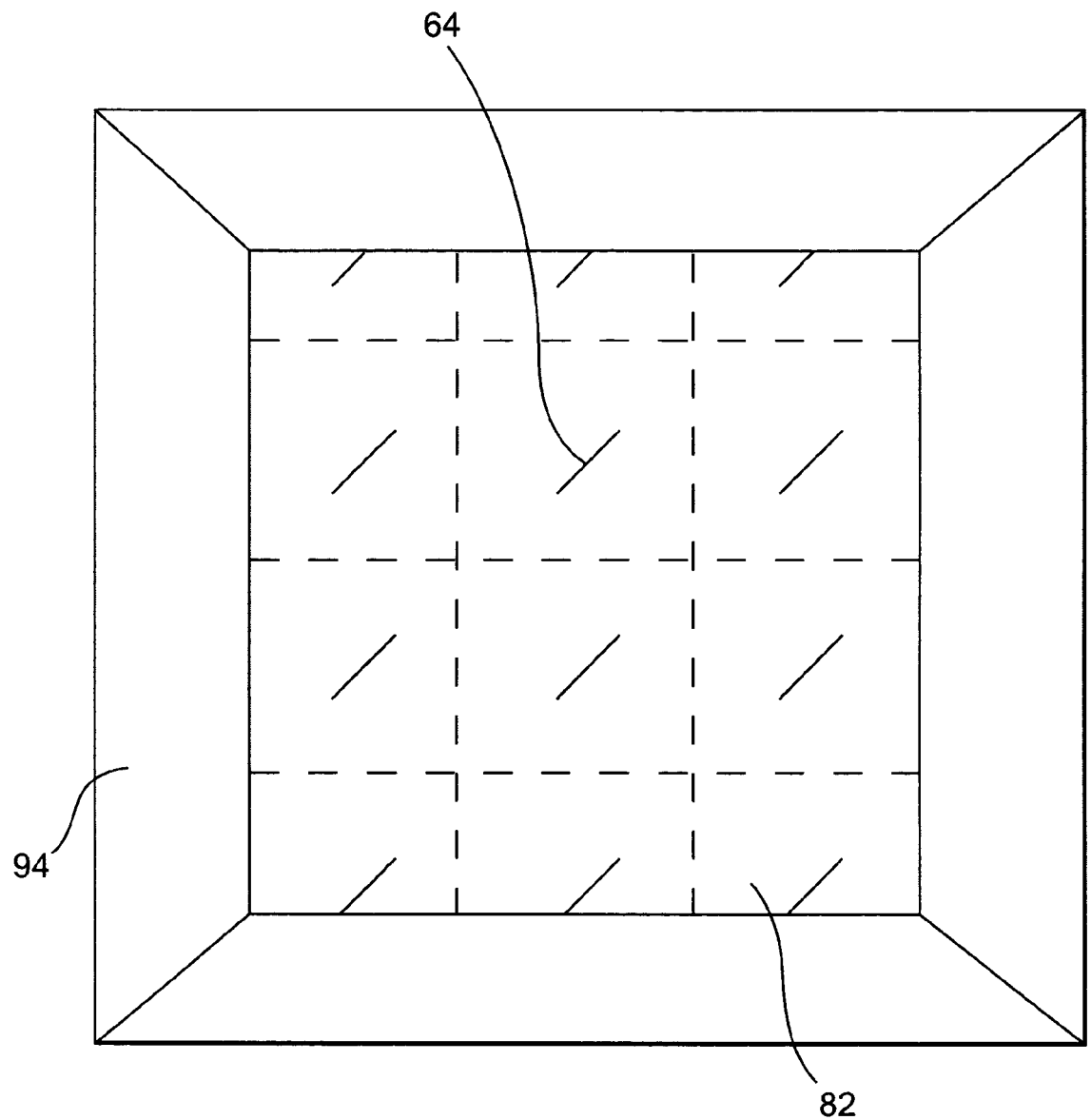
FIG. 12 is the bottom view of the cushion matrix of the first embodiment, showing a base carrier.

Referring to FIG. 12, base carrier 94 is attached, in one embodiment by sewing, to the outside edge of carrier matrix 82. Base carrier 94 is, in one embodiment, formed of similar material as bottom surface matrix 78 and is gathered in each corner to substantially constrict the opening formed at the bottom of base carrier 94.

Figure 10:
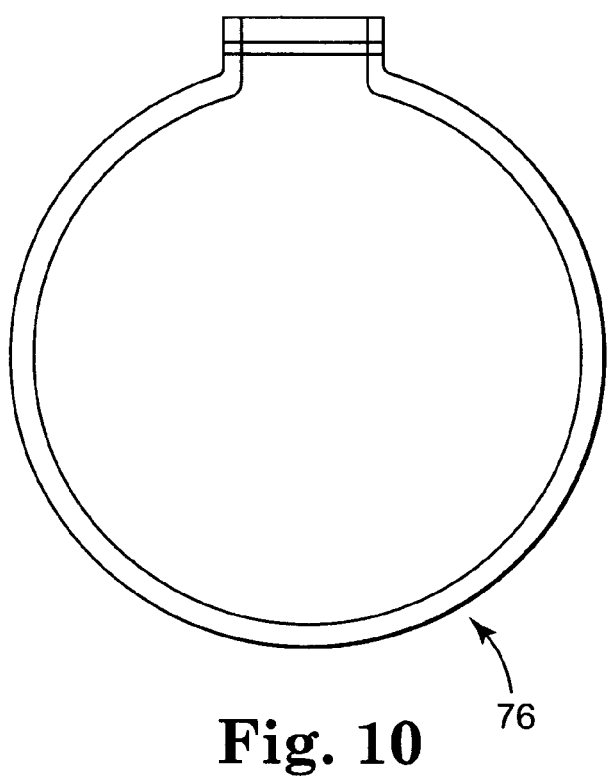
FIG. 10 is a side view of a cushion bladder of the first embodiment, designed to accept thermal transfer and/or cushion material and sized to fit within the primary or secondary interior volume of the cushion module carrier.

FIG. 10 shows a cushion element 76 of the present invention. Much like the thermal transfer element 74, the cushion element is a bladder typically constructed of a flexible, substantially moisture-impervious material such as urethane. Unlike the thermal transfer element, the cushion element is filled with a filler material which does not change phase, such as Floam or foam. In one embodiment, the amount of Floam foam in a cushion element varies with its location in the cushion matrix. Cushion elements closer to the support rails may be filled to a higher percentage of volume of the cushion element than cushion elements in the middle of the cushion. By varying the amount of fill of the cushion elements, a desired profile (such as a body matching contour) may be created Thermal transfer element 74 is typically located in the secondary interior volume 72 of cushion module carrier 62. Thermal transfer element 74 can be assembled into cushion module 60 by fitting it through aperture 64 and aperture 68 so that it is substantially seated in secondary interior volume 72. Cushion element 76 is typically located in primary interior volume 70 of cushion module carrier 62. Cushion element 76 can be assembled into cushion module 60 by fitting it through aperture 64 so that it is substantially seated in primary interior volume 70. Because the thermal transfer and cushion elements can be easily inserted and removed from the cushion element, they may be removed if a user wishes to launder the cushion module 60.

Alternatively, it may be preferable to locate and secure the thermal transfer element 74 and cushion member 76 within the cushion module. For example, thermal transfer element 74 and cushion element 76 may be attached to the cushion module with an adhesive or a stitch pattern. Further, thermal transfer element 74 and cushion element 76 may be attached to each other. Cushion module carrier 62 may be adapted to provide one or more internal volumes that are moisture impervious into which appropriate filler material may be added to create a thermal transfer and or a cushion element integral to the cushion module carrier. Other alterations or modifications to the cushion module to otherwise accommodate a thermal transfer element and a cushion element may be made without departing from the scope of the invention. The current design also allows for customization of the thermal or cushioning elements by removal or insertion of these elements to create the desired cushioning or temperature moderating effect. For example cushion elements 76 typically have a larger volume of filler material than thermal transfer elements 74. Thus, as arranged within the cushion as described above, when the user sits on the cushion, the weight of the users body tends to deform the cushion such that the transfer elements 74 are isolated from each other by portions of the cushion elements 76. This arrangement can be used to moderate the effect of the thermal transfer elements.

Figure 13:
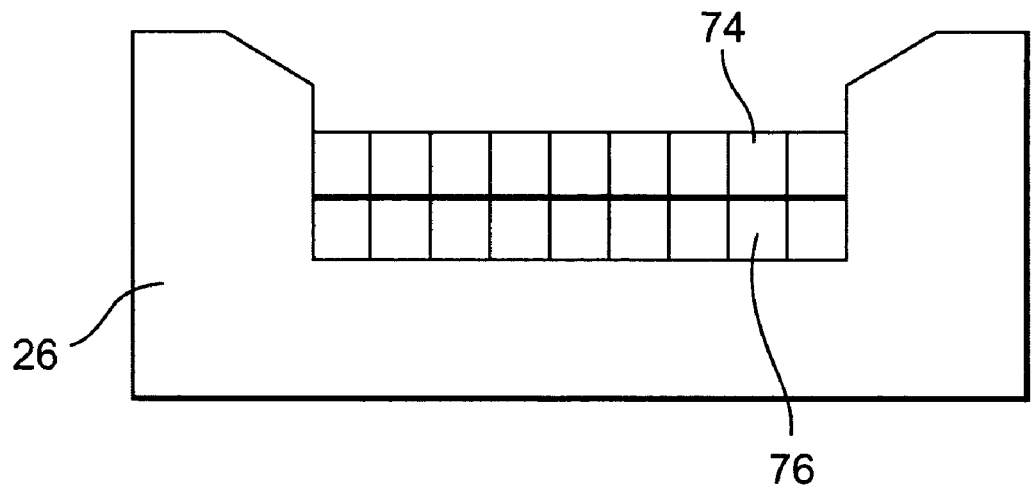
FIG. 13 is a second embodiment of the invention, showing a cushion matrix with a plurality of thermal transfer elements located atop a plurality of cushion elements.
Figure 14:
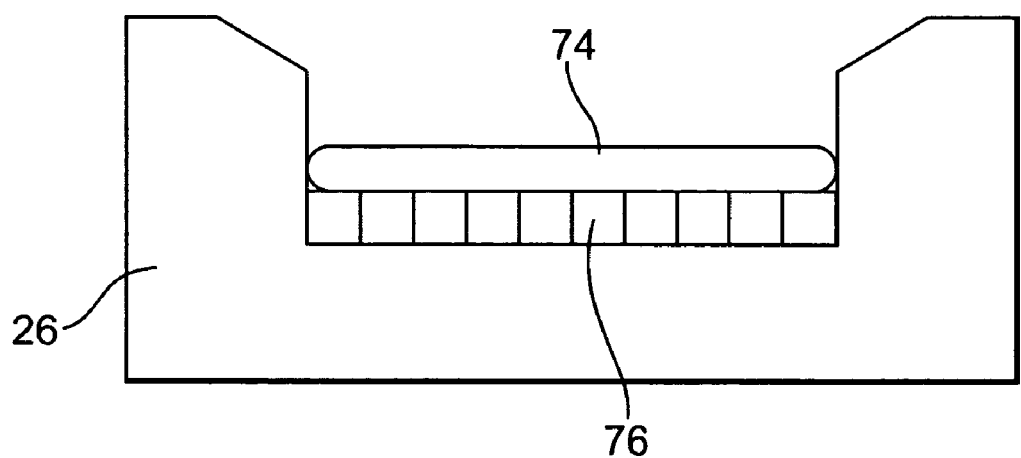
FIG. 14 is a third embodiment of the invention, showing a cushion matrix with a single thermal transfer element located atop a plurality of cushion elements.
Figure 15:
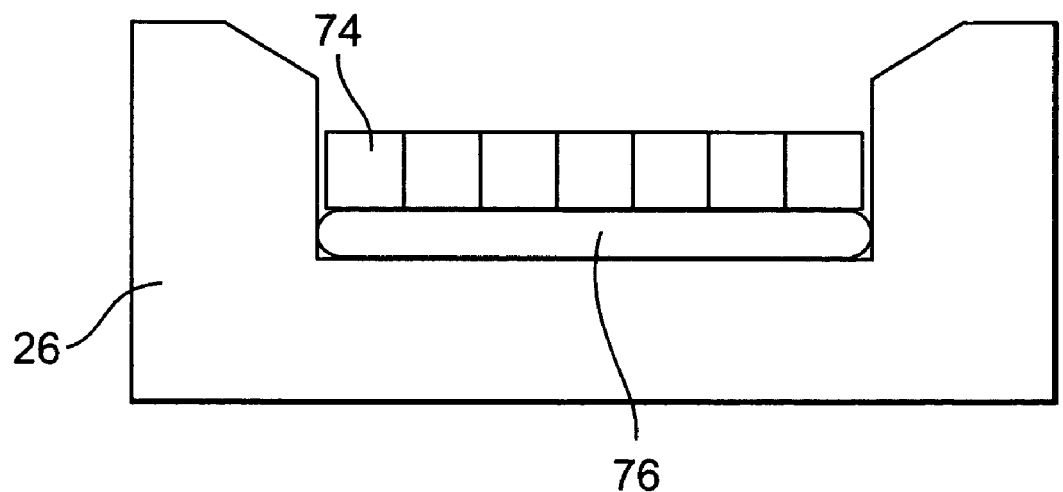
FIG. 15 is a fourth embodiment of the invention, showing a cushion matrix with a plurality of thermal transfer elements located atop a single cushion element.
Figure 16:
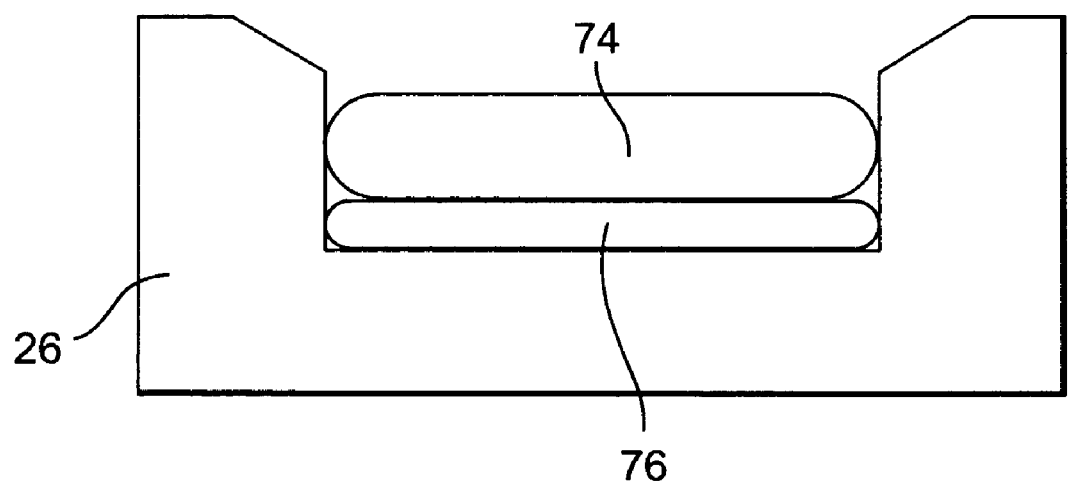
FIG. 16 is a fifth embodiment of the invention, showing a single thermal transfer element located atop a single cushion element.

FIGS. 13–16 show four additional embodiments of the inventive cushion. In FIG. 13, a plurality of cushion elements 76 are located upon cushion base 26, which in this embodiment includes a substantially homogeneous material, such as Ethafoam™. A plurality of heat transfer elements 74 is located above the cushion elements 76. In FIG. 14, a single heat transfer element 74 is located above a plurality of cushion elements 76. In FIG. 15, a plurality of heat transfer elements 74 is located above a single cushion element 76. In FIG. 16, a single heat transfer element 74 is located above a single cushion element 76. While each of these embodiments show a cushion base 26 made of a substantially homogeneous material, it is to be understood that these embodiments depicting alternate heat transfer and cushion elements may be combined with previously described cushion bases.

Embodiments of the present invention can utilize aspects present in a wheelchair cushion known commercially as the Cloud Cushion, which is offered by Otto Bock Healthcare (Minneapolis, Minn.). Details of the Cloud Cushion can be found at www.ottobockus.com and in publications by Otto Bock. Such details are hereby incorporated by reference.

Embodiments of the present invention can utilize Technogel™ material, for example, in place of or in conjunction with Floam™ material. Details regarding Technogel material can be found on the Internet at http://www.plastics.ottobock.com and from publications provided by Otto Bock. This material includes long polymer threads with only a few links and is strong and highly flexible at the same time.

All patents, patent applications and publications specified in this application are incorporated by reference in their entirety as if completely set out herein. While the present invention has been described with reference to preferred embodiments, workers skilled in the art will recognize that changes may be made in form and detail without departing from the scope of the invention.

TABLE 1

PARAFFINIC PCMS

| Paraffin | Number of | Melting Point | | Latent Heat of Fusion | Density at 20° C. |
|---|---|---|---|---|---|
| n-Alkanes | C Atoms | ° K | ° C. | (kJ/kg) | (kg/m') |
| Tetradecane | 14 | 278.95 | 5.8 | 227 | 759 (l) |
| Pentadecane | 15 | 283.05 | 9.9 | 207 | 765 (1) |
| Hexadecane | 16 | 291.25 | 18.1 | 236 | 770 (1) |
| Heptadecane | 17 | 295.05 | 21.9 | 214 | 775 (s) |
| Octadecane | 18 | 301.25 | 28.1 | 244 | 779 (s) |
| Nonadecane | 19 | 305.15 | 32 | 222 | 782 (s) |
| Eicosane | 20 | 309.75 | 36.6 | 248 | 785 (s) |
| Heneicosane | 21 | 313.35 | 40.2 | 213 | 788 (s) |
| Docosane | 22 | 317.15 | 44 | 252 | 791 (s) |
| Tricosane | 23 | 320.65 | 47.5 | 234 | 793 (s) |
| Tetracosane | 24 | 323.75 | 50.6 | 255 | 796 (s) |
| Pentacosane | 25 | 326.65 | 53.5 | 238 | 798 (s) |
| Hexacosane | 26 | 329.45 | 56.3 | 250 | 800 (s) |
| Heptacosane | 27 | 331.95 | 58.8 | 235 | 802 (s) |
| Octacosane | 28 | 334.35 | 61.2 | 254 | 803 (s) |
| Nonacosane | 29 | 336.35 | 63.2 | 239 | 805 (s) |
| Triacontane | 30 | 338.55 | 65.4 | 252 | 806 (s) |
| Hentriacontane | 31 | 341.05 | 67.9 | 242 | 808 (s) |
| Dotriacontane | 32 | 342.85 | 69.7 | 266 | 809 (s) |
| Tritriacontane | 33 | 344.55 | 71.4 | 256 | 810 (s) |
| Tetratriacontane | 34 | 346.25 | 73.1 | 268 | 811 (s) |
| Pentatriacontane | 35 | 347.85 | 74.7 | 257 | 6–12 (s) |
| Hexatriacontane | 36 | 349.35 | 76.2 | 269 | 814 (s) |
| Heptatriacontane | 37 | 350.85 | 77.7 | 259 | 815 (s) |
| Octatriacontane | 38 | 352.15 | 79 | 271 | 815 (s) |

TABLE 2

NON-PARAFFINIC PCMs

| Name | Melting Point °K | Melting Point °C. | Latent Heat of Fusion (kj/kg) | Density (kg/m3) | Description |
|---|---|---|---|---|---|
| Myristic acid, ethyl ester | 284 | 11 | 184 | | Non-paraffin organic |
| Acetic acid | 289.9 | 16.7 | 187 | 1050 | Non-paraffin organic |
| Glycerol | 291.1 | 17.9 | 198.7 | 1260 | Non-paraffin organic |
| Caprylic-Lauric | 292.25 | 19.1 | | | Non-paraffin organic |
| Caprylic-Myristic | 294.55 | 21.4 | | | Non-paraffin organic |
| Caprylic-Palmitic | 295.25 | 22.1 | | | Non-paraffin organic |
| Lactic Acid | 299 | 26 | 184 | 1249 | Non-paraffin organic |
| Caprylic-Stearic | 299.95 | 26.8 | | | Non-paraffin organic |
| Caprylic acid | 303.25 | 30.1 | 168.7 | | Non-paraffin organic |
| Lauric-Myristic | 305.75 | 32.6 | | | Non-paraffin organic |
| Lauric-Palmitic | 305.95 | 32.8 | | | Non-paraffin organic |
| Lauric-Stearic | 310.45 | 37.3 | | | Non-paraffin organic |
| Myristic-Palmitic | 312.95 | 39.8 | | | Non-paraffin organic |
| Lauric Acid | 314.45 | 41.3 | | | Non-paraffin organic |
| Myristic-Stearic | 317.15 | 44 | | | Non-paraffin organic |
| Elaidic Acid | 320 | 47 | 218 | 851 | Non-paraffin organic |
| Camphene | 323 | 50 | 238 | 812 | Non-paraffin organic |
| OxazolineWax-ES-254 | 323 | 50 | | | Non-paraffin organic |
| Palmitic-Stearic | 323.55 | 50.4 | | | Non-paraffin organic |
| Palmitic acid | 328 | 55 | 163 | 850 | Non-paraffin organic |
| Hpophosphoric acid | 328 | 55 | 213 | | Non-paraffin organic |
| Tristearin | 329 | 56 | 190.8 | 862 | Non-paraffin organic |
| Myristic acid | 331 | 58 | 199 | 858 | Non-paraffin organic |
| Beeswax | 335 | 61.8 | 177 | 950 | Non-paraffin organic |
| p-Chloraniline | 342 | 69 | 156 | 1213 | Non-paraffin organic |
| Stearic acid | 342.6 | 69.4 | 199 | 847 | Non-paraffin organic |
| Oxazoline Wax-TS-970 | 347 | 74 | | | Non-paraffin organic |
| 3-Bromo-d-camphor | 350 | 77 | 174 | 1449 | Non-paraffin organic |
| Polyethylene Glycol 600 | 293–298 | 20–25 | 146 | 1100 | Non-paraffin organic |
| Trimyristin | 306–330 | 33–57 | 201–213 | | Non-paraffin organic |
| Jojoba Wax | 284.65 | 11.5 | | | Insoluble fatty of natural oils and waxes |
| Caster Oil | 286.15 | 13 | | | Insoluble fatty of natural oils and waxes |
| Almond | 286.69 | 13.5 | | | Insoluble fatty of natural oils and waxes |
| Walnut | 287.45 | 14.3 | | | Insoluble fatty of natural oils and waxes |
| White Mustard Seed | 288.65 | 15.5 | | | Insoluble fatty of natural oils and waxes |
| Black Mustard | 289.65 | 16.5 | | | Insoluble fatty of natural oils and waxes |
| Esparto | 290.65 | 17.5 | | | Insoluble fatty of natural oils and waxes |
| Rape Seed (Canola) | 292.15 | 19 | | | Insoluble fatty of natural oils and waxes |
| Candlenut | 293.65 | 20.5 | | | Insoluble fatty of natural oils and waxes |
| Poppy Seed | 293.65 | 20.5 | | | Insoluble fatty of natural oils and waxes |
| Sunflower | 296.15 | 23 | | | Insoluble fatty of natural oils and waxes |
| Beechnut | 296.65 | 23.5 | | | Insoluble fatty of natural oils and waxes |
| Coconut Oil | 298.15 | 25 | | | Insoluble fatty of natural oils and waxes |
| Soy Bean Oil | 300.15 | 27 | | | Insoluble fatty of natural oils and waxes |
| Cotton Seed Stearin | 301.65 | 28.5 | | | Insoluble fatty of natural oils and waxes |
| Cotton Seed Oil | 307.65 | 34.5 | | | Insoluble fatty of natural oils and waxes |
| Pumpkin Seed | 331.15 | 58 | | | Insoluble fatty of natural oils and waxes |
| $NH_4Cl.Na_2SO_4.10H_2O$ | 284.25 | 11.1 | 165 | | Salt Hydrates |
| $NaCl.NH_4Cl.2Na_2SO_2.20H_2O$ | 285.95 | 12.8 | 173 | | Salt Hydrates |
| $NaCl.Na_2SO4.10H_2O$ | 291.45 | 18.3 | 175 | | Salt Hydrates |
| Calcium Chloride Hexahydrate | 302.6 | 29.4 | 170 | | Salt Hydrates |
| Sodium Sulfate | 305.6 | 32.4 | 253 | 1460 | Salt Hydrates |

TABLE 2-continued

NON-PARAFFINIC PCMs

| Name | Melting Point °K | Melting Point °C. | Latent Heat of Fusion (kj/kg) | Density (kg/m3) | Description |
|---|---|---|---|---|---|
| Decahydrate Sodium Carbonate Decalyhydrate | 306 | 33 | 251 | 1440 | Salt Hydrates |
| Calcium Bromide Hexahydrate | 306.95 | 33.8 | | | Salt Hydrates |
| Sodium Thiosulfate Pentahydrate | 322 | 49 | 200 | 86 | Salt Hydrates |
| Witco 85010-1 | 280.15 | 7 | >150 | | Crystalline alkyl hydrocarbons |
| Witco K-51 | 290.15 | 17 | >150 | | Crystalline alkyl hydrocarbons |
| Witco K-61 | 297.15 | 24 | >150 | | Crystalline alkyl hydrocarbons |
| Witco 45A | 304.15 | 31 | >150 | | Crystalline alkyl hydrocarbons |
| Kenwax 18 | 297–299 | 24–26 | | | Crystalline alkyl hydrocarbons |
| Kenwax 19 | 301–304 | 28–31 | | | Crystalline alkyl hydrocarbons |
| Kenwax 20 | 309.15 | 36 | | | Crystalline alkyl hydrocarbons |

What is claimed is:

1. A cushion for a wheelchair, the cushion comprising:
a cushion matrix, wherein the cushion a matrix includes
    a plurality of first cushion members wherein each first cushion member includes an amount of deformable filler material and an enclosure constructed of a flexible, moisture-resistant material that is formed to create an internal volume to accept and surround the filler material;
    at least one second cushion member wherein the at least one second cushion member includes an amount of a filler material including an encapsulated phase change material, and an enclosure constructed of a flexible, moisture-resistant material that is formed to create an internal volume to accept and surround the amount of filler material; and
    at least one support rail cushion; and
    a cushion member carrier, formed of a flexible material, shaped to accept and enclose each first cushion member, each of the at least one second cushion member and the support rail cushion; and
    a cushion base member.

2. The cushion of claim 1, wherein the cushion has an identical number of first cushion members and second cushion members.

3. The cushion of claim 2, wherein one first cushion member has a different amount of filler material from another first cushion member.

4. The cushion of claim 2, wherein the first cushion member has a first major surface and the second cushion member has a second major surface and wherein the cushion member carrier includes a plurality of cushion compartments, each of which is sized and shaped to accept at least one first cushion member and at least one second cushion member, wherein each compartment is constructed to allow at least one first cushion member and at least one second cushion member to be positioned such that the first major surface is adjacent to the second major surface.

5. The cushion of claim 4, wherein the cushion compartments are arranged so that each cushion compartment is adjacent to at least one other cushion compartment.

6. The cushion of claim 4, wherein each cushion compartment includes one first cushion member and one second cushion member.

7. The cushion of claim 6, wherein the cushion has a top surface and the second cushion member is positioned closer to the top surface of the cushion than the first cushion member.

8. The cushion of claim 2, wherein the amount of filler material located within the second cushion member has a volume less than a volume of filler material located within the first cushion member.

9. A cushion having top, bottom, left, right, front and back surfaces for use in a wheelchair, wherein the cushion has a depth defined as a distance from the front surface to the back surface, a width defined as a distance from a left surface to the right surface and a thickness defined as a distance from the top surface to the bottom surface, wherein the cushion is positionable in a seating area of the wheelchair such that the front surface is proximal to a front portion of the seating area and the back surface is proximal to a back portion of the seating area, and wherein the bottom surface the cushion contacts with a top surface of the seating area of the wheelchair and the top surface of the cushion is positioned to accept a user when the user is seated upon the wheelchair, the cushion comprising:
    a base, wherein the base has left, right, front, back, top and bottom surfaces that are oriented similarly substantially the same depth and width as the cushion, and the bottom surface of the base is substantially flat, wherein the base includes a first base member, formed of a polymer, generally rectangular in shape, located near the bottom surface of the base, sized to extend substantially along the width and depth of the cushion, wherein a thickness of the first base member has a constant dimension along a significant portion of the depth of the cushion and has a taper on the top of the lower base member so that a thickness of the lower base member varies along a significant portion of the width of the cushion;
    a second base member, located above the first base member, wherein a thickness of the second base member is substantially constant along a significant portion of the depth of the cushion and has a taper along a significant portion of the width of the cushion on the bottom of the upper base member such that the taper of the upper base member interfaces and complements the taper of the lower base member; and an outer base member, having a generally u-shape with an inside surface which is adjacent to the left, right, and back surfaces of the lower and upper base members and an outside surface which forms the left, right and back surfaces of the base, a bottom surface which forms a part of the bottom surface of the base, and a top surface which has a taper wherein the thickness of the top surface at the inside surface is at least as much as the thickness of the lower and upper surfaces and wherein the thickness of the outer base member increases as to a maximum thickness at the outside surface of outer base member;

a cushion matrix comprising a plurality of individual cushion bladders, wherein each individual cushion bladder includes
    a first cushion member comprised of a filler material;
    a second cushion member, located above and adjacent to the first cushion member, wherein the second cushion member is substantially isolated from the first cushion member, and wherein the second cushion member includes a heat transfer structure comprised of an encapsulated phase change material and a fill material;

a support rail comprising a plurality of individual support bladders, wherein each of the individual bladders includes a compartment, comprising filler material, and wherein the individual bladders are attachable and detachable from the base and are arranged to extend along the left, right, and back edges of the cushion so as to substantially surround the cushion matrix along the left, right, and back edges; and an envelope, which provides the external surfaces of the cushion wherein the base, cushion matrix and support rail are located within a volume of the envelope and are arranged so that the base member is substantially closer to the bottom of the cushion than the cushion matrix and support rail.

10. The cushion of claim 9, wherein the first base member is securely attached to the outer base member to provide a pevlic captivation structure.

11. The cushion of claim 9, wherein the first and second base members are connected to each other through use of an adhesive and enclosed within a pouch.

12. The cushion of claim 9, wherein the support rail is shaped and positioned to include a structure on the back edge of the cushion to provide sacrum relief.

13. The cushion of claim 9, wherein at least one of the individual bladders that comprise the support rail has an exterior surface that is attached to itself along acrosssectional area of the bladder so as to pinch the bladder and at least partially restrict movement of the filler material within the bladder.

14. The cushion of claim 9, wherein the phase change material is comprised of octadecane paraffin.

15. The cushion of claim 9, wherein the phase change material has a melting point of greater than 28 degrees Celsius.

16. The cushion of claim 9, wherein the phase change material has a re-crystallization point of less than 28 degrees Celsius.

* * * * *